(12) United States Patent
Geske

(10) Patent No.: US 7,494,672 B2
(45) Date of Patent: Feb. 24, 2009

(54) USE OF GUAIAC WOOD FOR TREATING INFLAMMATION OF THE SKIN

(76) Inventor: Gundula Geske, Rinnenwag 71, Owen 73277 (DE)

( * ) Notice: Subject to any disclaimer, the term of this patent is extended or adjusted under 35 U.S.C. 154(b) by 0 days.

(21) Appl. No.: 11/716,790

(22) Filed: Mar. 9, 2007

(65) Prior Publication Data

US 2007/0231417 A1    Oct. 4, 2007

(30) Foreign Application Priority Data

Mar. 9, 2006   (DE) .................. 10 2006 011 011
Sep. 11, 2006  (DE) .................. 10 2006 042 536

(51) Int. Cl.
*A61K 36/00*    (2006.01)
*A01N 33/18*    (2006.01)

(52) U.S. Cl. ...................... 424/725; 514/727
(58) Field of Classification Search ........................ None
See application file for complete search history.

(56) References Cited

FOREIGN PATENT DOCUMENTS

| EP | 0 265 662 A2 | 9/1987 |
|---|---|---|
| GB | 2 067 899 A | 8/1981 |
| JP | 09-255551 A * | 9/1997 |
| JP | 10158126 A | 6/1998 |
| WO | WO 87/06833 | 11/1987 |
| WO | WO 01/95728 A1 | 12/2001 |

OTHER PUBLICATIONS

Zusammenfassung; XP-002440736; "*Anti-acne Composition Plant Oil, especially Related to Composition Containing Plant Essential Oil with Excellent Anti-bacterial Activity to Propionibacterium Acnes and Skin Safety*"; Derwent Publications Ltd., London; 2006.

Zusammentassung; WP-002440737; "*Melanogenesis Inhbitor for Skin-has Specified Amounts of Extracts of Various Plants Combined With Low Petroleum and Organic Solvents*"; Derwent Publications Ltd., London; 1999.

Zusammenfassung; WP-002440738; "*External Compositions for Skin Treatment-Contain Extracts of Zygophylaceae Family Larrea and Guaiacum Genera, Particluarly Larrea Divaricata, Guaiacum Officinale and/or G. Sanctum*"; Dewent Publications Ltd., London; 1997.

Wolters, Bruno; XP-002440729; "*Immunstimulantien in der Indianischen Medizin*"; http://bibllpl.rz.tu-bs.de; Jul. 3, 2007. Abstract only.

* cited by examiner

*Primary Examiner*—Christopher R. Tate
(74) *Attorney, Agent, or Firm*—Morris Manning Martin LLP; Tim Tingkang Xia

(57) ABSTRACT

One aspect of the present invention relates to the use of an extract from guaiac wood to produce a pharmaceutical composition for treating inflammations of the skin. Another aspect of the present invention relates to the use of an extract from guaiac wood as a cosmetic.

15 Claims, 1 Drawing Sheet

USE OF GUAIAC WOOD FOR TREATING INFLAMMATION OF THE SKIN

FIELD OF THE INVENTION

The present invention relates to the use of an extract from guaiac wood to produce a pharmaceutical composition for treating inflammations of the skin. The present invention further relates to the use of an extract from guaiac wood as a cosmetic.

BACKGROUND OF THE INVENTION

The guaiac tree is one of the widespread yoke leaf plants (zygophyllaceae) in the tropics and subtropics and is a native of the West Indian islands as well as of the countries on the north coast of South America. The wood of the guaiac tree has been used for a long time as a traditional medicine by indian tribes of Middle and South-America. The wood reached Spain at the beginning of the 16th century and spread from where to the rest of Europe where it was initially used as "Lignum sanctum" (holy wood) especially for syphilis. In the course of time guaiac wood was also administered for the treatment of numerous other diseases above all for rheumatic diseases, arthritis, asthma, tuberculosis and malaria. Applications for the treatment of smallpox gave the tropical wood among others the popular name "pockwood". Ramos et al. (Arch. Med. Res. 1992; 23, 59-64) additionally describe a pronounced hypoglycaemic effect for an extract from *Guajacum coulteri*.

Guaiac wood consisting of the heartwood and the sapwood contains guaiac resin as the main active ingredient which is stored in the wood in zones resembling irregular annual rings. The heartwood contains up to 25% resin whereas only 2 to 3% resin is present in the sapwood. This resin is composed of various colophonic acids of the furoguaiacin type ($\alpha+\beta$ guaiaconic acid) and lignan type (guaiaretic acid and guaiacinic acid) as well as the phenol guaiacol. Other active ingredients of guaiac wood include essential oils (guaiac wood oil) which is mainly composed of the sesquiterpene alcohol guaiol, alkaloids and triterpene saponins with the aglycone oleanolic acid.

Whereas the ingredients of guaiac resin have a diuretic and diaphoretic effect, the fungicidal action of an extract of guaiac wood is due to the saponins contained in the wood. Guaiac oil has anti-inflammatory, antiseptic and wound healing promoting properties. In the food industry guaiac resin is used as an antioxidant to preserve above all animal fats. Since, guaiac resin is also a sensitive chemical reagent to oxidases and peroxidases, it is additionally used to detect blood in urine and faeces (haemoccult test). This detection of an occult blood is based on the oxidation of $\alpha$-guaiaconic acid to the quinoid guaiac blue (furoguaiacin blue).

Although an application of guaiac wood or of guaiac resin has been described in connection with numerous medical indications but in particular as part of a homeopathic treatment of rheumatic diseases, there are no studies whatsoever in the literature on the effect of such an extract in humans which would satisfy today's standards or could be rated as relevant. In particular there are no indications whatsoever in the literature for an application of an extract from guaiac wood to treat inflammations of the skin.

GB 2 067 899 A describes cosmetic compositions for treating the skin and/or hair which contain a powder of plant origin obtained from extraction residues of various plants. Guaiac wood (Lignum vitae) is mentioned as one of the plants from which such an extraction residue can be obtained by extracting therapeutically and/or cosmetically active substances with water or organic solvents.

EP 0 265 662 A2 discloses pharmaceutical agents which are pressed together from components of various plants cut up into small pieces and can be used to treat a diversity of diseases such as for example cardiovascular diseases, angina pectoris, psoriasis, allergic dermatitis, chronic infections, bronchial asthma and hepatitis. In this connection a composition is described among others which also contains guaiac wood (Guaiacum officinale) in a comminuted form in addition to a number of other components.

JP 10158126 A discloses a hair cosmetic which in addition to at least one antimicrobial compound, contains one or more compounds selected from the group comprising lecithin, ascorbic acid, erythorbic acid, guaiac resin, nordihydro-guaiaretic acid, gallus acid, a salt of ascorbic acid, a salt of erythorbic acid and a salt of nordihydroguairetic acid.

SUMMARY OF THE INVENTION

As a result of the continuously increasing need to fall back on products of natural origin to treat inflammations of the skin, it was an object of the present invention to provide an alternative to synthetic or other natural products which has an identical or similar spectrum of action.

This object is achieved according to the invention by the use of an extract from guaiac wood which is administered in a suitable formulation as a pharmaceutical composition.

The present invention concerns the use of an extract from guaiac wood to produce a pharmaceutical composition for treating inflammations of the skin.

The invention additionally concerns the use of an extract from guaiac wood as a cosmetic.

DETAILED DESCRIPTION OF THE INVENTION

Figure 1:
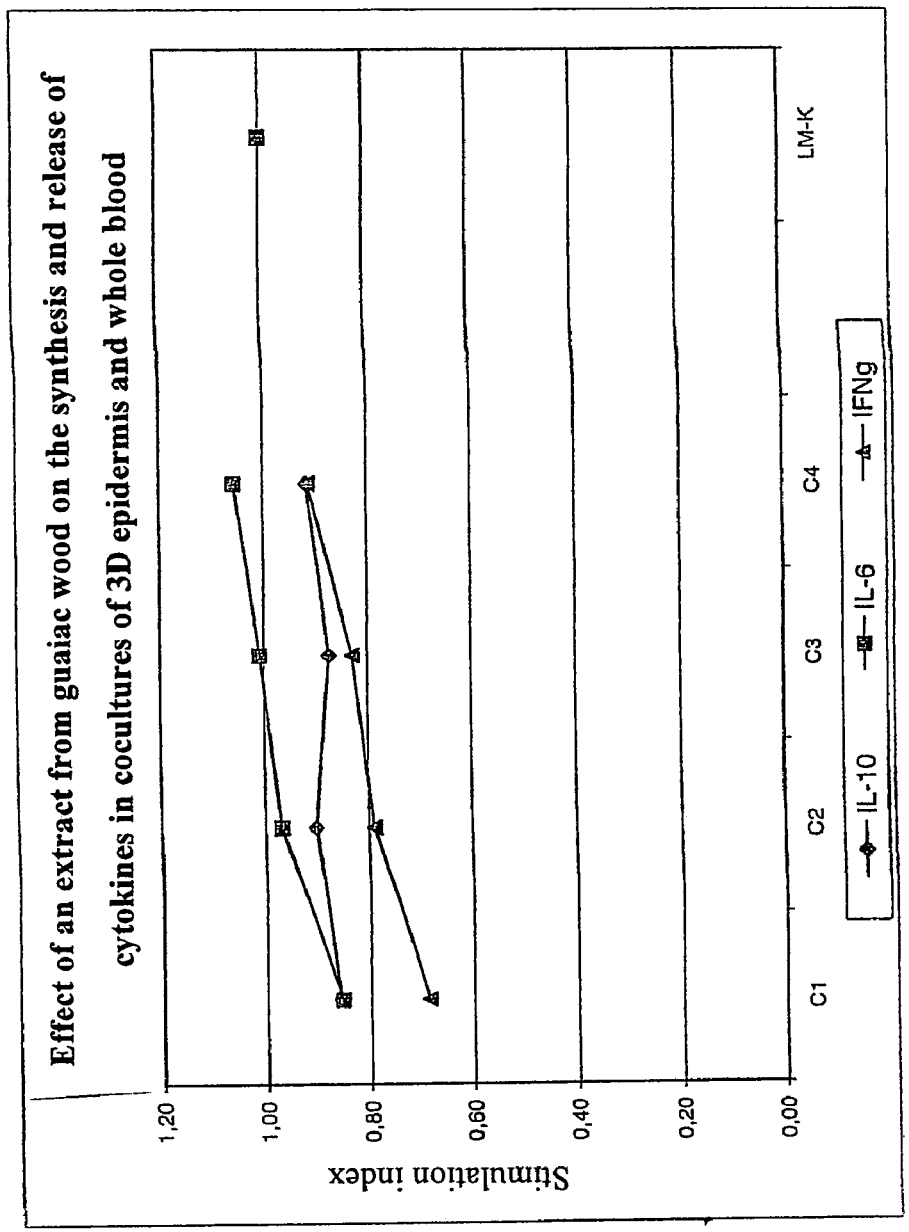
FIG. 1 shows effects of an extract from guaiac wood on the synthesis and release of cytokines in cocultures of 3D epidermis and whole blood.

It was surprisingly found within the scope of the present invention that an extract from guaiac wood is particularly suitable for treating inflammations of the skin. As shown by test results, after the active ingredients have been absorbed through the skin, an extract from guaiac wood inhibits the release of interferon gamma (IFNγ) an important cytokine for the development and maintenance of inflammatory processes (see example in connection with FIG. 1). The most important producers of this messenger are type 1 T helper cells (Th1) which play an important role among others in the pathogenesis of rheumatic diseases (Berner et al., J. Rheumatol. 2000, 27, 1128-1135; Vervoordeldonk et al., Curr. Rheumatol. Rep. 2002, 4, 208-217) as well as in the chronification of atopic dermatitis (Lugovic et al., Int. Arch. Allergy Immunol. 2005, 137, 125-133; Biedermann et al., J. Investig. Dermatol. Symp. Proc. 2004, 9, 5-14) and the pathogenesis of psoriasis (Szegedi et al., Immunol. Lett. 2004, 86, 277-280).

Thus especially the IFNγ-inhibitory activity of an extract from guaiac wood is used according to the invention.

The extract is produced preferably by extracting guaiac wood with water, an aliphatic alcohol with 1 to 6 carbon atoms or combinations thereof. More preferably a mixture of water and an aliphatic alcohol with 2 to 4 carbon atoms is used as the extracting agent. The extracting agent is particularly preferably aqueous ethanol (70% v/v).

In agreement with the invention the compositions disclosed in the present application comprise the extract from guaiac wood described above preferably in an amount of 1 to 50%, more preferably of 5 to 40% and most preferably of 10 to 30% based on the total weight of the pharmaceutical composition.

In a preferred embodiment the pharmaceutical composition of the present invention comprises the extract from guaiac wood in combination with one or more pharmaceutically acceptable carriers, thickeners, humectants and/or additives where the term "pharmaceutically acceptable carrier" refers to one or more liquid, semi-solid or solid diluents, fillers or other substances which are suitable for administration to mammals including humans.

The term "pharmaceutically acceptable" as used herein refers to any non-toxic material which does not impair the effectiveness of the biological activity of the active ingredient. Such materials can include pharmaceutically acceptable concentrations of salts, buffers, preservatives or suchlike where in the case of medical applications the salts should be pharmaceutically acceptable salts. Use of non-pharmaceutically acceptable salts would be conceivable provided pharmaceutically acceptable salts can be produced from such salts.

The term "carrier" in the sense of the present invention refers to any organic or inorganic, natural or synthetic substance which can be combined with the active ingredient to simplify the administration. Examples of such carriers include but are not limited to organic or inorganic solvents, starch, lactose, mannitol, methylcellulose, talcum, gelatine, agar-agar, calcium phosphate, magnesium stearate, animal and vegetable fats, high molecular weight fatty acids or high molecular weight polymers.

Preferred pharmaceutically acceptable carriers in the sense of the present invention are liquid carriers such as water, aqueous salt solutions, non-aqueous (anhydrous) solvents or mixtures thereof. Suitable non-aqueous solvents include but are not limited to ethanol, propanol, isopropanol, butanol, benzyl alcohol, glycerol, propylene glycol, di- or tripropylene glycol, polyethylene glycol, methylcellosolve, cellosolve, morpholine, dioxane, N,N-dimethylformamide, dimethylsulfoxide, tetrahydrofuran, phthalates, adipates or esters. In a particularly preferred embodiment the carrier used comprises water.

The compositions according to the invention can additionally contain one or more thickeners. Examples of thickeners which can be used within the scope of the present invention include in particular organic polymers. The thickeners are preferably water-soluble thickeners such as cellulose derivatives where hydrophilically modified cellulose derivatives such as hydroxyethyl cellulose, hydroxypropyl cellulose, carboxymethyl cellulose and/or hydroxypropylmethyl cellulose are particularly preferred. Particularly suitable organic polymers in the sense of the present invention are also mucopolysaccharides such as hyaluronic acid or other glycosaminoglycans. In another particularly preferred embodiment the thickener can be a polyacrylic acid which can be preferably cross-linked and/or chemically modified, or be a salt of such a polyacrylic acid. Preferred polyacrylic acids are cross-linked acrylic acid polymers e.g. acrylic acid homopolymers, copolymers or interpolymers or salts of such polymers e.g. alkaline or alkaline earth salts. These for example include carbomer homopolymers i.e. high molecular weight polymers of acrylic acid which are cross-linked with polyalkenyl ethers of sugars or polyalcohols such as allylsucrose, allylpentaerythritol etc. e.g. Carbopol® 940 NF, 974P NF or 980 NF. The following are also suitable: carbomer copolymers i.e. high molecular weight copolymers of acrylic acid and $C_1$-$C_{24}$ alkylmethacrylates cross-linked with polyalkenyl ethers of sugars or polyalcohols such as Carbopol® 1382, Carbopol® 1342 NF, Carbopol® ETD-2020, Pemulen® TR1 NF and Pemulen® TR2 NF. Carbopol® Ultrez 10, 20 or 21 or Carbopol® Ultrez 10 NF come for example into consideration as carbomer interpolymers i.e. carbomer homopolymers or copolymers which contain a heterologous polymer e.g. a block copolymer of polyethylene glycol and a long-chain e.g. $C_1$-$C_{24}$ alkyl acid ester.

According to the invention the pharmaceutical composition of the present application can additionally contain one or more suitable humectants. Preferred examples of humectants are pharmaceutically acceptable polyalcohols such as propylene glycol, in particular 1,2-propylene glycol, pentylene glycol, in particular 1,2-pentanediol, glycerol and/or polyethylene glycol.

Additives in the sense of the present invention for example include reagents for adjusting the pH, buffers, diluents, processing aids such as emulsifiers, preservatives, stabilizers, antioxidants, light protecting agents, dyes and suchlike. In particular compounds of alkali or alkaline earth metals giving a basic reaction such as hydroxides, hydrogen carbonates, carbonates etc are preferably used as reagents to adjust the pH which among others also include organometallic compounds. Likewise it is also possible, if appropriate, to use acids including organic and inorganic acids to adjust the pH. Suitable buffers include, but are not limited to acetic acid, citric acid, tartaric acid, boric acid or phosphoric acid in combination with their corresponding bases. Preservatives which can be used within the scope of the present invention include, but are not limited to benzalkonium chloride, chlorobutanol, thiomersal or parabene.

In a preferred embodiment of the invention the pharmaceutical composition additionally contains dexpanthenol which plays an important role in skin metabolism and is metabolized in the body of mammals to pantothenic acid (vitamin B5).

The pharmaceutical compositions according to the invention are preferably formulated as a spray, gel, cream, ointment or lotion wherein a formulation as a cream, ointment or lotion is more preferred. However, the composition can also be administered in the form of aerosols, aqueous or non-aqueous solutions, foams, emulsions, suspensions or other suitable formulations.

The composition according to the invention is preferably administered topically. Other forms of administration which are suitable for administering compositions within the sense of the present invention are known to a person skilled in the field of pharmacology or medicine and include, but are not limited to subcutaneous, intradermal, transdermal, oral, nasal, inhalative, rectal or intravenous administration. The compositions according to the invention are administered such that per administration dose preferably an amount in the range of 10 mg to 10 g and particularly preferably an amount in the range of 100 mg to 1 g dry extract is provided. In a preferred embodiment the administered amount is a pharmaceutically effective amount.

According to the invention the compositions described in the present application are used for the treatment of inflammations of the skin. The term "treatment" used here refers to a therapeutic treatment in which the recipient is administered an amount of the compositions according to the invention that is effective for prevention, alleviation or elimination of inflammation or allergy.

Inflammations of the skin which can be treated by the compositions according to the invention can be caused by allergens, microorganisms and/or physical stimuli. In a preferred embodiment the allergens causing the inflammation are foreign allergens and more preferably inhalation allergens, ingestion allergens, contact allergens, injection allergens, invasion allergens and/or depot allergens. Alternatively the inflammation of the skin can also be caused by autoallergens.

Inhalation allergens include, but are not limited to plant and grass pollen, mould spores, house dust mite excrement, animal hairs, cereal and chemical dust or solvent vapours. Ingestion allergens include, but are not limited to foods (e.g. milk, fish, fruit, cereals, nuts) or medicines that have to be taken orally. Contact allergens include, but are not limited to chemicals, synthetic substances (e.g. plastics, disinfectants, drugs), metals, substances of animal origin (e.g. wool, silk) or substances of plant origin (e.g. resins). Injection allergens include, but are not limited to drugs, vaccines, vaccination sera as well as insect poisons. Invasion and depot allergens include, but are not limited to surgical implants or dental root filling materials.

The term "microorganisms" within the sense of the present invention encompasses bacteria, fungi, yeasts, protozoa, algae and viruses. The microorganisms causing the inflammation are preferably bacteria, fungi or viruses.

An inflammation of the skin can also be caused by physical stimuli which are of a mechanical, thermal and/or chemical nature. Mechanical stimuli include, but are not limited to pressure, injury, effects of foreign bodies or suchlike. Chemical stimuli include, but are not limited to acids, bases, toxins, enzymes that are out of control or suchlike. Heat and cold are thermal stimuli which can cause inflammation of the skin.

Inflammations of the skin which can be treated by the pharmaceutical compositions according to the invention include, but are not limited to dermatitis and psoriasis. In a preferred embodiment the dermatitis to be treated is atopic dermatitis.

The present invention additionally concerns the use of an extract from guaiac wood as a cosmetic and in particular as a skin cosmetic. The cosmetic is used for skin protection, skin care and skin cleansing and/or to improve the condition of the skin.

The present invention is further elucidated by the following example.

EXAMPLE

In order to evaluate the effect of an extract from guaiac wood, in vitro investigations were carried out on a test system relevant for dermatological compositions which enables an extensive simulation of the in vivo conditions. For this purpose an alcoholic extract from guaiac wood was added to a culture system consisting of three-dimensional, differentiated human epidermis and whole blood. The set-up of the test system was selected such that cells of the immune system and of the organ system that has a regulatory associated therewith were divided between two culture compartments so that a direct cell/cell contact was excluded but exchange of messengers was possible. The culture system was incubated with the extract in such a manner that the cells of the immune system could only come into contact with the active ingredients of the extract when the active ingredients were able to permeate through the intact epidermis.

FIG. 1 shows the effect of an extract from guaiac wood on the synthesis and release of cytokines from human leucocytes in cocultures of epidermis and whole blood. In this case a significant inhibition of the release of interferon gamma (IFNγ), an important cytokine from T cells for the development and maintenance of inflammatory processes, is observed. Furthermore, the release of interleukin 6 (IL-6) and interleukin 10 (IL-10) is inhibited to a slight extent.

What is claimed is:

1. A method for treating an inflammation of the skin, comprising the step of administering a pharmaceutically effective amount of a composition comprising an extract from guaiac wood and dexpanthenol to a patient in need thereof.

2. The method according to claim 1, characterized in that the inflammation is caused by at least one of allergens.

3. The method according to claim 2, characterized in that the allergens are at least one of foreign allergens and autoallergens.

4. The method according to claim 3, characterized in that the foreign allergens are at least one of inhalation allergens, ingestion allergens, contact allergens, injection allergens, invasion allergens and depot allergens.

5. The method according to claim 1, characterized in that the inflammation of the skin is at least one of dermatitis and psoriasis.

6. The method according to claim 5, characterized in that the dermatitis is an atopic dermatitis.

7. The method according to claim 1, characterized in that the pharmaceutical composition contains the extract from guaiac wood in an amount of 1 to 50% based on the total weight of the composition.

8. The method according to claim 1, characterized in that the pharmaceutical composition further comprises at least one of a pharmaceutically acceptable carrier, a thickener, a humectant and an additive.

9. The method according to claim 8, characterized in that the pharmaceutically acceptable carrier comprises water, an aqueous salt solution, a non-aqueous solvent or mixtures thereof.

10. The method according to claim 8, characterized in that the thickener comprises an organic polymer.

11. The method according to claim 10, characterized in that the organic polymer comprises at least one of a hydrophilically modified cellulose derivative, a mucopolysaccharide and a polyacrylic acid.

12. The method according to claim 11, characterized in that the polyacrylic acid comprises at least one of a cross-linked and chemically-modified polyacrylic acid.

13. The method according to claim 8, characterized in that the humectant comprises at least one of propylene glycol, pentylene glycol, glycerol and polyethylene glycol.

14. The method according to claim 1, characterized in that the pharmaceutical composition is formulated in the form of a spray, gel, cream, ointment or lotion.

15. The method according to claim 1, characterized in that the pharmaceutical composition is formulated for a topical administration.

* * * * *